(12) United States Patent
Chez

(10) Patent No.: US 7,456,224 B2
(45) Date of Patent: Nov. 25, 2008

(54) METHOD FOR TREATING AUTISM

(75) Inventor: Michael Gene Chez, Lake Bluff, IL (US)

(73) Assignee: Forest Laboratories Holdings, Ltd., Hamilton (BM)

(*) Notice: Subject to any disclaimer, the term of this patent is extended or adjusted under 35 U.S.C. 154(b) by 121 days.

(21) Appl. No.: 11/018,992

(22) Filed: Dec. 21, 2004

(65) Prior Publication Data

US 2005/0222272 A1   Oct. 6, 2005

Related U.S. Application Data

(60) Provisional application No. 60/559,651, filed on Apr. 5, 2004.

(51) Int. Cl.
*A01N 33/02* (2006.01)
*A01N 43/58* (2006.01)
*A01N 43/60* (2006.01)
*A01N 43/42* (2006.01)
*A61K 31/13* (2006.01)
*A61K 31/495* (2006.01)
*A61K 31/50* (2006.01)
*A61K 31/44* (2006.01)

(52) U.S. Cl. ................ 514/662; 514/659; 514/661; 514/289; 514/250

(58) Field of Classification Search ............. 514/250, 514/662, 659, 289, 661
See application file for complete search history.

(56) References Cited

U.S. PATENT DOCUMENTS

| | | | |
|---|---|---|---|
| 4,122,193 A | 10/1978 | Scherm et al. | |
| 4,273,774 A | 6/1981 | Scherm | |
| 4,994,467 A * | 2/1991 | Zimmerman | 514/284 |
| 5,061,703 A * | 10/1991 | Bormann et al. | 514/212.01 |
| 6,057,373 A | 5/2000 | Fogel | |
| 6,362,226 B2 * | 3/2002 | Phillips et al. | 514/568 |
| 2001/0044446 A1 | 11/2001 | Phillips et al. | |
| 2006/0167032 A1 * | 7/2006 | Galer et al. | 514/282 |

FOREIGN PATENT DOCUMENTS

| | | | |
|---|---|---|---|
| WO | WO 99/36064 A | | 7/1999 |
| WO | WO 03/061656 | * | 7/2003 |
| WO | WO 03/061656 A | | 7/2003 |
| WO | WO 2004/009062 | * | 1/2004 |
| WO | WO 2004/009062 A | | 1/2004 |
| WO | WO 2005/084655 A | | 9/2005 |
| WO | WO 2006/034187 A2 | | 3/2006 |
| WO | WO 2006/034465 A1 | | 3/2006 |

OTHER PUBLICATIONS

Autistic Spectrum Disorders, Fact Sheet.*
Chez, Michael G. et al.: "Neurologic treatment strategies in autism: An overview of medical intervention strategies"; Seminars in Pediatric Neurology, Saunders, Philadelphia, PA; vol. 11, No. 3, Sep. 2004 pp. 229-235, XP004666246, ISSN: 1071-9091.
Michael G. Chez et al., "Donepezil Hydrochloride: A Double-Blind Study in Autistic Children," Journal of Pediatric Neurology 2003; 1(2): 83-88.
Michael G. Chez et al., "Memantine as Add-On Therapy in Pediatric Epileptic Patients: Effects on Cognitive Developmental and Seizure Frequency," Abstract—American Epilepsy Society Abstract, Epilepsia 45 Suppl. 7:152 (Abst. 1.4.06), 2004.
Michael G. Chez et al., "Memantine Experience in Children and Adolescents with Autistic Spectrum Disorders," Abstract—Annals of Neurology, vol. 56, Supp. 8, S109, Sep. 2004.
Michael G. Chez et al., "Neurologic Treatment strategies in Autism: An Overview of Medical Intervention Strategies," Seminars in Pediatric Neurology, 229-235, 2004.
Bryan H. King et al., Double-Blind, Placebo-Controlled Study of Amantadine Hydrochloride in the Treatment of children with Autistic Disorder, J. Am. Acad. Child Adolesc. Psychiatry, 40:6 Jun. 2001.
C.G. Parsons et al., Memantine is a Clinically Well Tolerated N-Methyl-D-Aspartate (NMDA) Receptor Antagonist—a Review of Preclinical Data, Neuropharmacology 38 (1999) 735-767.
David J. Posey, M.D. et al., A Pilot Study of D-Cycloserine in Subjects with Autistic Disorder, Am J Psychiatry 2004; 161:2115-2117).
A.E. Purcell, et al. "Postmortem Brain Abnormalities of the Glutamate Neurotransmitter System in Autism," Neurology 2001; 57:1618-1628.
I.M. Sukhanov et al., "Effects of NMDA Receptor Channel Blockers, MK-801 and Memantine, on Locomotor Activity and Tolerance to Delay of Reward in Wistar-Kyoto and Spontaneously Hypertensive Rats," Behavioral Pharmacology, vol. 15, No. 4, 263-271, 2004.

* cited by examiner

*Primary Examiner*—Sreeni Padmanabhan
*Assistant Examiner*—Umamaheswari Ramachandran
(74) *Attorney, Agent, or Firm*—Finnegan, Henderson Farabow, Garrett & Dunner, L.L.P.

(57) ABSTRACT

A method for treating autism comprising the step of administering an effective amount of a medicament characterized as a NMDA-receptor antagonist or a pharmaceutically acceptable salt thereof.

4 Claims, No Drawings

METHOD FOR TREATING AUTISM

CROSS-REFERENCE TO RELATED APPLICATIONS

This application claims the benefit of U.S. Provisional Application Ser. No. 60/559,651 filed Apr. 5, 2004, entitled "MEMANTINE AS A TREATMENT FOR AUTISM AND AS THERAPY FOR COGNITIVE DECLINE DUE TO EPILEPSY" which is hereby incorporated herein by reference in its entirety, including all references cited therein.

BACKGROUND OF THE INVENTION

1. Field of the Invention

The present invention relates in general to a method for treating autism and, more particularly, to a method for treating autism via administering an effective amount of a NMDA-receptor antagonist or a pharmaceutically acceptable salt thereof.

2. Background Art

Autism is a complex developmental disability that interferes with, among other things, the normal development of the brain in the areas of social interaction and communication skills. It typically appears during the first three years of life and is the result of a neurological disorder which affects the functioning of the brain. Typically, autistic children and adults have difficulties in verbal and non-verbal communication, social interactions, and leisure or play activities.

According to the Autism Society of America (hereinafter the "ASA"), autism is generally characterized as one of five disorders coming under the umbrella of Pervasive Developmental Disorders (PDD), a category of neurological disorders characterized by severe and pervasive impairment in several areas of development, including social interaction and communications skills (DSM-IV-TR). The five disorders under PDD are Autistic Disorder, Asperger's Disorder, Childhood Disintegrative Disorder (CDD), Rett's Disorder, and PDD-Not Otherwise Specified (PDD-NOS). Specific diagnostic criteria for each of these disorders can be found in the Diagnostic & Statistical Manual of Mental Disorders (DSM-IV-TR) as distributed by the American Psychiatric Association (APA).

The most common of the Pervasive Developmental Disorders, autism affects an estimated 1 in approximately 200 births. Indeed, as of 2003-2004, as many as 1.5 million Americans are believed to have some form of autism. Such a number is on the rise inasmuch as, based on statistics from the U.S. Department of Education and other governmental agencies, autism is growing at a rate of 10-17 percent per year. At these rates, the ASA estimates that the prevalence of autism could easily reach 4 million Americans in the next decade.

The overall incidence of autism is, for the most part, globally consistent. Indeed, autism knows no racial, ethnic, or social boundaries, and family income, lifestyle, and educational levels do not affect the chance of autism's occurrence. However, it has been found to be four times more prevalent in boys than girls.

Since being first described by Dr. Leo Kanner in 1943, the understanding of autism has grown tremendously. However, the general public, and even many professionals in the medical, educational, and vocational fields, remain unaware of the effects of the disability and how to most effectively work with individuals having the disability. For example, autistic individuals may exhibit both positive and negative responses to their environment. Though some may find it surprising, many children and adults with autism may make eye contact, show affection, smile and laugh, and demonstrate a variety of other emotions, although in varying degrees.

Although autism is defined by a certain set of behaviors, it is a spectrum disorder in that its symptoms and characteristics can be present in a wide variety of combinations, from mild to severe. Therefore, autistic children and adults can exhibit any combination of the behaviors in any degree of severity. Two individuals, both with the same diagnosis, may have varying skills and display very different actions.

Indeed, every person with autism is an individual, and like all individuals, each has a unique personality and combination of characteristics. Those only mildly affected may exhibit slight delays in language or communication and may face greater challenges in social interactions. For example, one may have difficulty initiating and/or maintaining a conversation. Communication by autistic children or adults is often displayed as talking at others (for example, a monologue on a favorite subject that continues despite attempts by others to interject comments).

Autism requires those affected by it to process and respond to information in unique ways. At times, aggressive and/or self-injurious behavior may exist. The following traits, as identified by the ASA, may also be present in persons with autism: Insistence on sameness or resistance to change; Difficulty in expressing needs; (i.e. uses gestures or pointing instead of words); Repeating words or phrases in place of normal, responsive language; Laughing, crying, showing distress for reasons not apparent to others; Prefers to be alone or aloof manner; Tantrums; Difficulty in mixing with others; May not want to cuddle or be cuddled; Little or no eye contact; Unresponsive to normal teaching methods; Sustained odd play; Spins objects; Inappropriate attachments to objects; Apparent over-sensitivity or under-sensitivity to pain; No real fears of danger; Noticeable physical over-activity or extreme under-activity; Uneven gross/fine motor skills; and/or Not responsive to verbal cues (i.e. acts as if deaf although hearing tests in normal range).

For most people, our senses help us to understand what we are experiencing. For example, our senses of touch, smell, sound, and taste collaborate to give us a full experience of eating a ripe apple: the feel of the smooth skin as we pick it up, its sweet smell as we move it to our mouth, the crunch of the fruit being bitten into, and the juices running down our face as we enjoy the bite. For individuals with autism, however, sensory integration problems are common. In particular, their senses may be either over- or under-active. The fuzz of a kiwi may actually be experienced as painful; a sweet, fruity smell may cause a gagging reflex. Some children or adults with autism are particularly sensitive to sound, so that even the most ordinary daily noises are painful. Many professionals feel that some of the typical autism behaviors are actually a result of sensory integration difficulties.

Although there is no known single known cause for autism, it is generally accepted that it is caused by abnormalities in brain structure or function. The shape and structure of the brain in autistic versus non-autistic children show differences when brain scans are viewed. Currently the link between heredity, genetics and medical problems are being investigated by researchers, as well as a number of other theories. The theory of a genetic basis of the disorder is supported by the fact that, in many families, there appears to be a pattern of autism or related disabilities. While no one gene has been identified as causing autism, researchers are searching for irregular segments of genetic code that autistic children may have inherited. While researchers have not yet identified a single "trigger" that causes autism to develop, it also appears that some children are born with a susceptibility to autism.

Other researchers are investigating the possibility that under certain conditions, a cluster of unstable genes may interfere with brain development resulting in autism. Still other researchers are investigating problems during pregnancy or delivery as well as environmental factors such as viral infections, metabolic imbalances, and exposure to environmental chemicals.

According to the ASA, autism tends to occur more frequently than expected among individuals who have certain medical conditions, including Fragile X syndrome, tuberous sclerosis, congenital rubella syndrome, and untreated phenylketonuria (PKU). Some harmful substances ingested during pregnancy also have been associated with an increased risk of autism. Early in 2002, The Agency for Toxic Substances and Disease Registry (ATSDR) prepared a literature review of hazardous chemical exposures and autism found no compelling evidence for an association; however, there was very limited research and more needs to be done.

Whatever the cause, parents can rest assured that autism is not caused by bad parenting. Children with autism and PDD are either born with the disorder or with the potential to develop it. No known psychological factors in the development of the child have been shown to cause autism. Furthermore, autism is not a mental illness; autistic children are not unruly kids who choose not to behave.

Notwithstanding the foregoing, and to the best of Applicant's knowledge, there is no cure for autism. There are, however, a number of medications, developed for other conditions, which have been found to be somewhat helpful in treating a limited number of the symptoms and behaviors frequently found in individuals with autism, such as hyperactivity, impulsivity, attention difficulties, and anxiety. Examples of medications used to treat symptoms associated with autism include: Serotonin re-uptake inhibitors (e.g. clomipramine (Anafranil), fluvoxamine (Luvox) and fluoxetine (Prozac)) which have been effective in treating depression, obsessive-compulsive behaviors, and anxiety that are sometimes present in autism. Studies have shown that they may reduce the frequency and intensity of repetitive behaviors, and may decrease irritability, tantrums and aggressive behavior. Some children have shown improvements in eye contact and responsiveness. Other drugs, such as Elavil, Wellbutrin, Valium, Ativan and Xanax, require more studies to be done but may have a role in reducing behavioral symptoms.

Over the past 35 years, the most widely studied psychopharmacologic agents in autism have been anti-psychotic medications. Originally developed for treating schizophrenia, these drugs have been found to decrease hyperactivity, stereotypic behaviors, withdrawal and aggression in autistic children. Four that have been approved by the FDA are clozapine (Clozaril), risperidone (Risperdal), olanzapine (Zyprexa) and quetiapine (Seroquel). However, only risperidone has been investigated in a controlled study of adults with autism. Unfortunately, like the antidepressants, these drugs all have adverse side effects, including, but not limited to, sedation.

Stimulants, such as Ritalin, Adderall, and Dexedine, used to treat hyperactivity in children with ADHD have also been prescribed for children with autism. Although few studies have been done, they may increase focus, and decrease impulsivity and hyperactivity in autism, particularly in higher-functioning children. Unfortunately, adverse behavioral side effects are often observed.

While many of the above-identified medications do appear to be somewhat helpful in treating a limited number of the symptoms and behaviors frequently found in individuals with autism, a wide variety of side effects are associated with such medications.

It has now been surprisingly discovered that administering an effective amount of a NMDA-receptor antagonist or a pharmaceutically acceptable salt thereof appears to substantially improve frontal executive functions associated with autistic symptoms, including, but not limited to, speech expression and decreased perseveration. Furthermore, administering such a NMDA-receptor antagonist or a pharmaceutically acceptable salt thereof has not been shown to cause side effects associated with medications previously used to treat the symptoms of autism.

It is therefore an object of the present invention, to provide a method for treating autism via administering an effective amount of a NMDA-receptor antagonist or a pharmaceutically acceptable salt thereof.

SUMMARY OF THE INVENTION

The present invention is directed to a method for treating autism comprising the step of administering an effective amount of a medicament characterized as a NMDA-receptor antagonist or a pharmaceutically acceptable salt thereof.

In accordance with the present invention, the step of administering an effective amount of a medicament can include the step of administering an effective amount of a medicament represented by the following chemical structure:

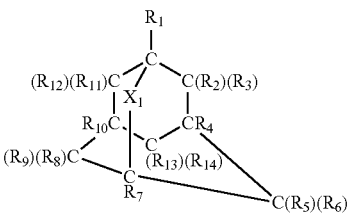

wherein $X_1$ comprises $CH_2$ or $R_{15}$; wherein $R_{1-15}$ are the same or different and comprise H, an amino group, a primary amine, a secondary amine, a tertiary amine, a quaternary ammonium group, a hydroxy group, a straight or branched alkyl, cycloalkyl, polycycloalkyl, heterocycloalkyl, aryl, alkaryl, aralkyl, alkoxy, alkenyl, alkynyl group containing approximately 1 to approximately 50 carbon atom(s), a silyl or siloxyl group containing approximately 1 to approximately 50 silicon atom(s), and combinations thereof.

Preferably, the step of administering an effective amount of a medicament includes the step of administering an effective amount of a medicament represented by the following chemical structure:

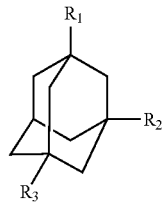

wherein $R_{1-3}$ are the same or different and comprise H, an amino group, a primary amine, a secondary amine, a tertiary amine, a quaternary ammonium group, a hydroxy group, a straight or branched alkyl, cycloalkyl, polycycloalkyl, heterocycloalkyl, aryl, alkaryl, aralkyl, alkoxy, alkenyl, alkynyl group containing approximately 1 to approximately 50 carbon atom(s), a silyl or siloxyl group containing approximately 1 to approximately 50 silicon atom(s), and combinations thereof.

In yet another preferred embodiment of the present invention, the step of administering an effective amount of a medicament includes the step of administering an effective amount of a medicament represented by the following chemical structure:

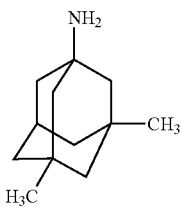

In accordance with the present invention, the step of administering an effective amount of a medicament may include the step of administering an effective amount of a medicament represented by the following chemical structure:

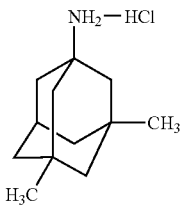

In another preferred embodiment of the present invention, the step of administering an effective amount of a medicament includes the step of administering an effective amount of 1-amino-3,5-dimethyladamantane hydrochloride and pharmaceutically acceptable derivatives thereof.

Preferably, the step of administering an effective amount of medicament includes the step of administering the medicament in a concentration ranging from approximately 1 mg to approximately 100 mg per day.

In yet another preferred embodiment of the present invention, the step of administering an effective amount of medicament includes the step of administering the medicament in a concentration ranging from approximately 5 mg to approximately 20 mg per day.

The present invention is also directed to a method for treating autism comprising the step of administering an effective amount of a medicament represented by the following chemical structure:

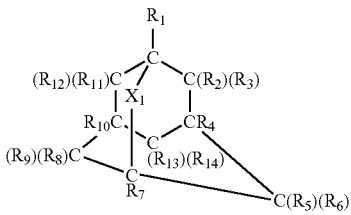

wherein $X_1$ comprises $CH_2$ or $R_{15}$; wherein $R_{1-15}$ are the same or different and comprise H, an amino group, a primary amine, a secondary amine, a tertiary amine, a quaternary ammonium group, a hydroxy group, a straight or branched alkyl, cycloalkyl, polycycloalkyl, heterocycloalkyl, aryl, alkaryl, aralkyl, alkoxy, alkenyl, alkynyl group containing approximately 1 to approximately 50 carbon atom(s), a silyl or siloxyl group containing approximately 1 to approximately 50 silicon atom(s), and combinations thereof, and wherein the step of administering the medicament includes the step of administering the medicament in a concentration ranging from approximately 5 mg to approximately 20 mg per day.

The present invention is further directed to a method for treating autism comprising the step of administering an effective amount of a medicament characterized as a NMDA-receptor antagonist or a pharmaceutically acceptable salt thereof; wherein the step of administering an effective amount of a medicament includes the step of administering an effective amount of 1-amino-3,5-dimethyladamantane hydrochloride and pharmaceutically acceptable derivatives thereof; and wherein the step of administering an effective amount of medicament includes the step of administering the medicament in a concentration ranging from approximately 5 mg to approximately 20 mg per day.

DETAILED DESCRIPTION OF THE INVENTION

While this invention is susceptible of embodiment in many different forms, there will herein be described in detail several specific embodiments with the understanding that the present disclosure is to be considered as an exemplification of the principles of the invention and is not intended to limit the invention to the embodiments illustrated.

In accordance with the present invention, a method for treating autism is disclosed which comprises the step of administering an effective amount of a medicament characterized as a NMDA-receptor antagonist or a pharmaceutically acceptable salt thereof. Preferably, the NMDA-receptor antagonist is a moderate affinity NMDA-receptor antagonist. It will be understood that regardless of its ordinary meaning the term "moderate" will be defined in accordance with the comprehensive teachings as disclosed by Merz in its Brief Profile of Memantine available from the internet at http://www.memantine.com/en/brief_profile/, which is hereby incorporated herein by reference in its entirety.

In one embodiment of the present invention, the medicament is represented by the following chemical structure:

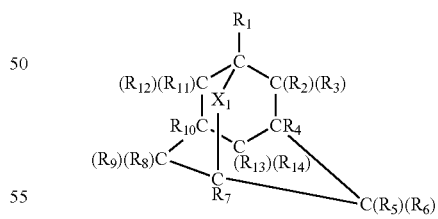

wherein $X_1$ comprises $CH_2$ or $R_{15}$; wherein $R_{1-15}$ are the same or different and comprise H, an amino group, a primary amine, a secondary amine, a tertiary amine, a quaternary ammonium group, a hydroxy group, a straight or branched alkyl, cycloalkyl, polycycloalkyl, heterocycloalkyl, aryl, alkaryl, aralkyl, alkoxy, alkenyl, alkynyl group containing approximately 1 to approximately 50 carbon atom(s), a silyl or siloxyl group containing approximately 1 to approximately 50 silicon atom(s), and combinations thereof.

In a second embodiment of the present invention, the medicament is represented by the following chemical structure:

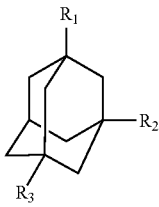

wherein $R_{1-3}$ are the same or different and comprise H, an amino group, a primary amine, a secondary amine, a tertiary amine, a quaternary ammonium group, a hydroxy group, a straight or branched alkyl, cycloalkyl, polycycloalkyl, heterocycloalkyl, aryl, alkaryl, aralkyl, alkoxy, alkenyl, alkynyl group containing approximately 1 to approximately 50 carbon atom(s), a silyl or siloxyl group containing approximately 1 to approximately 50 silicon atom(s), and combinations thereof.

In a third embodiment of the present invention, the medicament is represented by the following chemical structure:

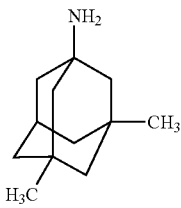

and may, specifically, comprise the hydrochloride salt provided herein below represented by the following chemical structure:

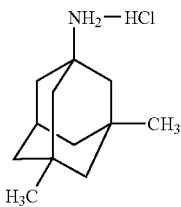

For purposes of clarity, and in an attempt to eliminate any potential ambiguity associated with the nomenclature of the above-identified medicament, it will be understood that the specific medicament provided herein above is defined as 1-amino-3,5-dimethyladamantane hydrochloride, which is commercially available from Merz under the trade name Memantine.

It will be understood that an "effective amount" of one or more above-identified medicament(s) can be administered, via any one of a number of conventional means, to an autistic patient/subject. Preferably, the effective dose ranges in concentration from approximately 1 milligram (mg) to approximately 100 mg per day, and more preferably ranges in concentration from approximately 5 mg to approximately 20 mg per day. However, the effective amount will vary depending upon the weight of the patient/subject.

In support of the present invention, an experiment was conducted to evaluate the use of Memantine in children and adolescents with autistic spectrum disorders (hereinafter referred to as "ASD"). Memantine, has been found to improve cognitive function by reducing the neuronal signal-to-noise ratio as one mechanism of action. A range of 2.5-10 mg per day of Memantine was applied as an open-label trial in children with ASD. Clinical observations of global function in language and/or behavior patterns were assessed.

Thirty patients, including 24 males and 6 females with an average age of 8.92 years and meeting DSM-IV criteria for ASD, were treated with Memantine for greater than 8 weeks. The patients were evaluated using a global clinical improvement scale rating for improvement in language and behaviors based on parental observation and clinical appearance. Improvements were rated as follows: moderate to significant, mild to moderate, or no improvement. The therapy ranged from between 8 to 40 weeks, with an average duration of therapy of 18 weeks and an average daily dosage of 8.1 mg.

After the thirty patients were treated for more than 2 months with Memantine, parents reported improvements in 26 of the 30 patients in one or more categories: attention, motor planning, language function (both receptively and expressively), and self-stimulatory behaviors. Moderate to significant improvement occurred in 16 of the 26, with milder improvement in 10 of the 26. No side effects were reported.

While further controlled studies in ASD with Memantine can be beneficial to follow up on these observations, Memantine appears to clearly improve frontal executive functions, including better attention, improved speech expression, and decreased perseveration.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A method of treating autism comprising administering to a patient in need thereof an effective amount of 1-amino-3,5-dimethyladamantane or a pharmaceutically acceptable salt thereof, wherein the 1-amino-3,5-dimethyladamantane or a pharmaceutically acceptable salt thereof is administered in a dosage ranging from approximately 1 mg to approximately 100 mg per day.

2. The method according to claim 1, wherein the 1-amino-3,5-dimethyladamantane or a pharmaceutically acceptable salt thereof is administered in a dosage ranging from approximately 5 mg to approximately 20 mg per day.

3. The method according to claim 1, wherein the is 1-amino-3,5-dimethyladamantane is a hydrochloride salt.

4. The method according to claim 3, wherein the 1-amino-3,5-dimethyladamantane hydrochloride salt is administered in a dosage ranging from approximately 5 mg to approximately 20 mg per day.

* * * * *

UNITED STATES PATENT AND TRADEMARK OFFICE
CERTIFICATE OF CORRECTION

PATENT NO. : 7,456,224 B2
APPLICATION NO. : 11/018992
DATED : November 25, 2008
INVENTOR(S) : Michael Gene Chez It is certified that error appears in the above-identified patent and that said Letters Patent is hereby corrected as shown below:

In claim 3, column 8, line 55, after "wherein the" delete "is".

Signed and Sealed this

Third Day of March, 2009

JOHN DOLL
*Acting Director of the United States Patent and Trademark Office*